United States Patent [19]

Sestak et al.

[11] Patent Number: 4,562,047
[45] Date of Patent: Dec. 31, 1985

[54] INDICATOR SEAL AND STERILIZER CONTAINER

[75] Inventors: Joseph T. Sestak, Erie; Jonathan Kagan, Fairview, both of Pa.

[73] Assignee: American Sterilizer Company, Erie, Pa.

[21] Appl. No.: 562,971

[22] Filed: Dec. 19, 1983

[51] Int. Cl.$^4$ ............................................. A61L 2/06
[52] U.S. Cl. ..................................... 422/300; 220/214; 292/318; 292/322; 422/26; 422/119; 422/310; 436/1
[58] Field of Search ................. 422/26, 119, 310, 300; 436/1; 292/318, 322; 220/214

[56] References Cited

U.S. PATENT DOCUMENTS

| | | | |
|---|---|---|---|
| 3,290,080 | 12/1966 | Dawson | 292/322 |
| 3,360,339 | 12/1967 | Edenbaum | 422/26 X |
| 3,523,011 | 8/1970 | Bhiwandker et al. | 436/1 X |
| 3,712,655 | 1/1973 | Fuehrer | 292/322 X |
| 3,717,369 | 2/1973 | Stoffel et al. | 292/322 X |
| 4,091,921 | 5/1978 | Lewis | 422/119 X |
| 4,179,397 | 12/1979 | Rohowetz et al. | 422/119 X |
| 4,331,257 | 5/1982 | Tascher | 220/214 X |
| 4,457,327 | 7/1984 | Pepper | 422/310 X |
| 4,506,921 | 3/1985 | Swift | 292/318 |

FOREIGN PATENT DOCUMENTS 2375869  7/1978  France .

*Primary Examiner*—David L. Lacey
*Assistant Examiner*—B. P. Heaney
*Attorney, Agent, or Firm*—Robert D. Yeager

[57] ABSTRACT

A sterilizer container includes a seal member so positioned on the container that movement of the outer cover of the container to a contaminating position requires fracturing the seal, thereby destroying the utility of the seal member and thus providing a visual indication that the articles within the container are contaminated. Further, the seal member includes a sterilization indicator which provides a further indication that the articles contained within the container are sterile.

3 Claims, 29 Drawing Figures

INDICATOR SEAL AND STERILIZER CONTAINER

BACKGROUND OF THE INVENTION

1. Field of the Invention

The present invention pertains to containers for sterilizing and storing articles and, more particularly, to a sterilizer container that provides an indication of whether the articles within the container should be considered sterile.

2. Description of the Prior Art

It is often necessary for medical personnel to store sterilized articles in such a manner that their sterilized state is maintained during storage. To facilitate sterilizing and storing the articles, workers in the art have developed containers in which the articles are both sterilized and subsequently stored in their sterilized state. Generally, the containers permit entry of the sterilizing medium into the container during performance of the sterilization process, but prevent the entry of microbial life into the container.

Sterilizer containers containing sterile articles commonly are left unattended for a relatively long period of time before the articles are used. There exists the possibility that the container will be opened while it is in storage, causing contamination of the articles, and subsequently reclosed. Such unauthorized opening is often prompted by a desire to steal for personal use articles disposed in the container. Visual inspection of the container and articles does not necessarily reveal the contaminated state of the articles. Therefore, hospital personnel must either assume the risk of using contaminated articles where sterile articles are needed, or bear the burden of following involved procedures to positively restrict access to the containers. Such procedures are not employed due to their impracticality. Of course, locks can be used to deter unauthorized tampering with the containers. However, the requirement of a key to gain access to the interior of the container limits the number of authorized persons who are able to gain access to the interior of the container. Further, a lock provides no indication that the container has been opened and reclosed and, therefore, provides no indication whether the articles in the container are sterile.

As a consequence, a sterilizer container has been developed which maintains a vacuum within the container upon completion of the sterilization cycle. Opening the container defeats the vacuum. Thus, absence of a vacuum within the sterilizer container indicates that the articles within the container are contaminated. However, it is not possible to determine whether the articles have been contaminated by observing the closed container. Further, it is necessary to transport a container to a sterile environment before checking for a vacuum to avoid contaminating the articles when the container is opened.

Accordingly, there exists a need for a container in which articles can be sterilized and subsequently stored, and which provides a visual indication of whether the container has been opened subsequent to sterilization.

Further, although there exist many types of fracturable seals which can be used to provide an indication of whether a container has been opened, applicant is not aware of a seal which includes a process indicator.

SUMMARY OF THE INVENTION

The present invention provides a container for holding articles while they are being subjected to a sterilization process, for storing the articles subsequent to the completion of the sterilization process, and for maintaining the degree of sterilization of the article achieved during the course of the sterilization process. The container includes a receptacle adapted to receive and support the articles while they are being stored and sterilized. A closure is provided which is capable of assuming an opened position, in which access can be had to the receptacle to permit the receptacle to receive articles and to permit removal of articles from the receptacle, and a closed position, in which such access cannot be had. Apparatus is provided for permitting the flow of the sterilizing medium or sterilant, into the receptacle while preventing the entry of microbial life into the receptacle when the closure is in its closed position. A disposable sealing member is so secured to the container that movement of the closure from its closed position to a contaminating position, in which microbial life can enter the receptacle, causes the seal to fracture and, thus, lose its ability to function as a seal.

The sealing member further includes a sterilization indicator.

The present invention also provides a disposable seal that indicates whether the container to which it is secured has undergone a sterilization process. The seal has a body portion connected to a fracturable portion. The fracturable portion is adapted to be so mounted to a container that opening the container requires fracturing the seal and, thus, destroying its utility as a seal. The seal includes a sterilization portion defined by the seal which includes a sterilization indicator. The sterilization indicator is, preferably, incorporated into the material itself, carried by tape which is taped to the seal, or is simply applied directly to the material of the seal.

Therefore, the present invention provides a sterilization container which indicates with a high degree of assurance whether the articles inside the container are sterile or contaminated. Further, the present invention provides a sealing device that provides an indication of whether the container that it seals has been exposed to a sterilization process.

BRIEF DESCRIPTION OF THE DRAWINGS

For a better understanding of the invention, reference may be had to the preferred embodiments, exemplary of the invention, shown in the accompanying drawings in which.

DETAILED DESCRIPTION OF THE PREFERRED EMBODIMENTS

FIGS. 21 through 28 show a preferred embodiment of the indicator seal provided by the present invention. Indicator seal 126 includes a body 130 and a fracturable member 124. Body 130 defines indicator portion 131, which is connected to a pair of supports 133 and 134. Fracturable member 124 is either secured to or formed integrally with support 133. Support 134 either defines or supports a lock 136. Lock 136 defines a locking passage 135, which is adapted to receive and secure within passage 135 a locking member 137 defined by the unsupported end of fracturable member 124. When locking member 137 is inserted fully within locking passage 135, end 138, defined by locking member 137, passes completely through locking passage 135 and is prevented from being withdrawn from locking passage 135 by end 129 of locking passage 135, which bears against shoulder 141 defined by locking member 137.

Indicator portion 131 includes sterilization indicators 132. Indicators 132 can be any known indicator suitable for the sterilization process to which the seal will be subjected. The indicators 132 can be printed directly on portion 131 or it can be applied to adhesive backed tape which is secured to portion 131. Alternately, indicators 132 can be a portion of indicator portion 131 that is constructed of a plastic which changes its appearance upon exposure to a sterilization process.

FIGS. 18 through 20 and FIG. 29 show the preferred embodiments of the sealed sterilizer container provided by the present invention. Generally, each sealed sterilizer container includes a sterilizer container and an indicator seal. The sterilizer container can be any suitable known container that permits gas to flow from the exterior to the interior of the container, but prevents the entry of microbial life. The sterilizer containers shown in FIGS. 1 through 17 are particularly suitable for use with the preferred embodiment of the present invention and are disclosed in application for U.S. Letters Patent Ser. No. 442,179, filed Nov. 16, 1982.

All the containers shown in the drawings include a lower container portion (or receptacle) 10, an outer cover or closure 12 and an intermediate cover 14. In the container shown in FIGS. 1–4, the intermediate cover 14 has perforations 16 formed therein; perforations 16 are covered by an overlying filter material 18. Filter material 18 may be formed of well-known materials that permit the passage of sterilizing media and air but prevent the passage of microbial contamination. Examples of such materials are nonwoven polyolefins, which are disposable, and 280 count muslin, which is reusable. In the containers shown in FIGS. 5 and 6, the intermediate cover 14a is nonperforated and has at least one two-way valve 20 installed therein. Valve 20 may be constructed in accordance with West German Pat. No. 12 17 551. In either case, intermediate covers 14, 14a ideally are interchangeable within outer cover 12.

Figure 1:
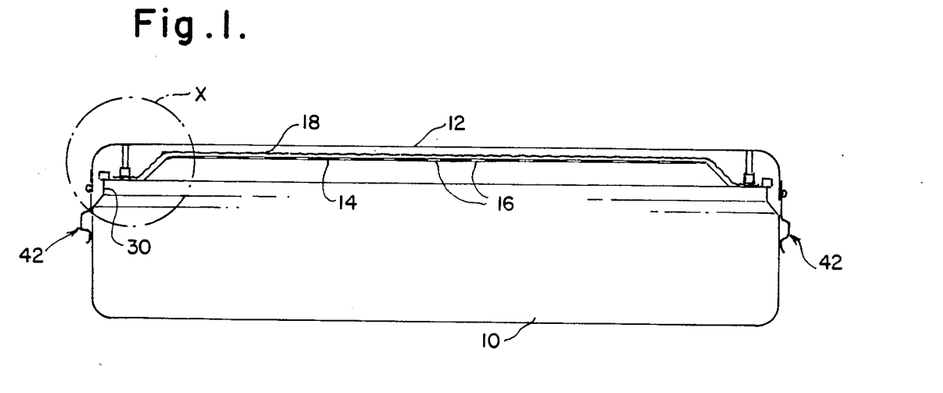
FIG. 1 is a sectional view of a sterilization container having a filter.
Figure 2:
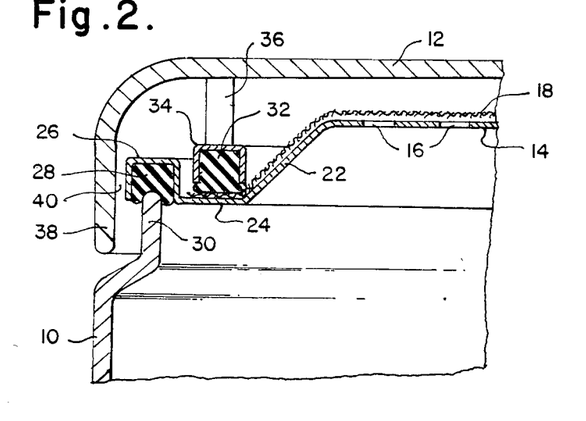
FIG. 2 is an enlarged sectional view of that portion of the container of FIG. 1 located within the circle x.

Referring to intermediate cover 14, as depicted in FIGS. 1–4, the major flat central portion contains perforations 16; proceeding toward the edges, intermediate cover 14 has an inclined transition segment 22, a flat segment 24, and terminates in an inverted U-shaped segment 26. U-shaped segment 26 is adapted to receive a sealing ring or gasket 28. In assembled condition, sealing ring 28 rests on the inwardly drawn upper edge 30 of container base portion 10. Sealing ring 28 seals the interior of container base portion 10 against the passage of microbial contamination in accordance with well-known principles. Alternatively, sealing ring 28 could be attached to upper edge 30 of container base portion 10 to form a seal with a corresponding surface of intermediate cover 14. In the container shown in FIG. 2, a sealing means against the passage of microbial contamination around filter material 18 and into container base portion 10 is shown; that sealing means includes a series of downwardly extending posts 36 (only one of which is shown in FIG. 2) from the lower surface of outer cover 12. Posts 36 terminate in an inverted U-shaped segment 34 which receives sealing ring 32. The openings between posts 36 permit the free flow of sterilizing media and air. Intermediate cover 14 is releasably attached to outer cover 12 by means of screw-joints or snap closures (not shown). When outer cover 12 is placed over intermediate cover 14, seal 32 presses filter 18 in a sealing manner against flat segment 24 of intermediate cover 14. As can be seen best in FIGS. 2–4, outer cover 12 with its downwardly extending sides 38 overlaps inwardly drawn edges 30 of container base portion 10, thereby leaving an annular gap 40 through which the media exchange between the environment surrounding the sterilizer container and the interior of container base portion 10 takes place. This arrangement, however, prevents the insertion of any objects which could damage filter 18 (or a valve as shown in FIG. 5). This arrangement further provides a tortuous path for the flow of media between the outside environment and the interior of container base portion 10. When outer cover 12 is securely fastened on container base portion 10 by means of a tension lock 42 (see FIG. 5), the interior of container base portion 10 is sealed off against microbial contamination in the manner described above. Further, the sealing ring 32 is pushed onto intermediate cover 14 and, because of the elasticity of sealing ring 32, various thicknesses of filter material 18 may be accommodated.

Figure 3:
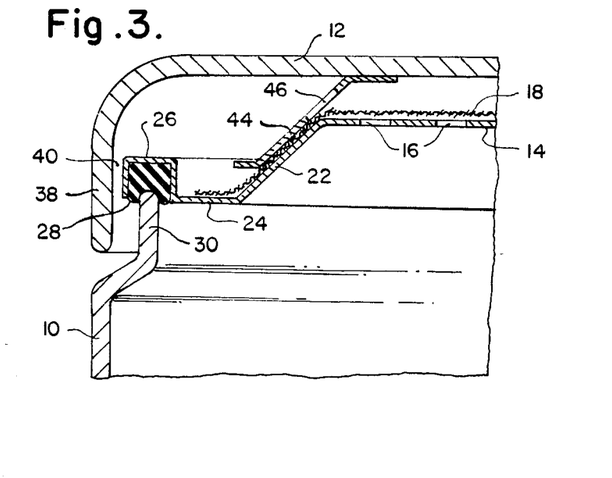
FIG. 3 is an enlarged sectional view, similar to FIG. 2, of a portion of another sterilization container.

With respect to the container shown in FIG. 3, posts 36 and their associated sealing ring 32 are eliminated and replaced by a peripheral spring plate 44 which is attached to outer cover 12. Spring plate 44 is configured to conform with inclined transition segment 22 of intermediate cover 14. Spring plate 44 includes openings 46 to allow for the media exchange. The lower portion of spring plate 44 rests against filter material 18 when outer cover 12 is securely in place and presses filter material 18 against inclined transition segment 22 to effect a seal.

Figure 4:
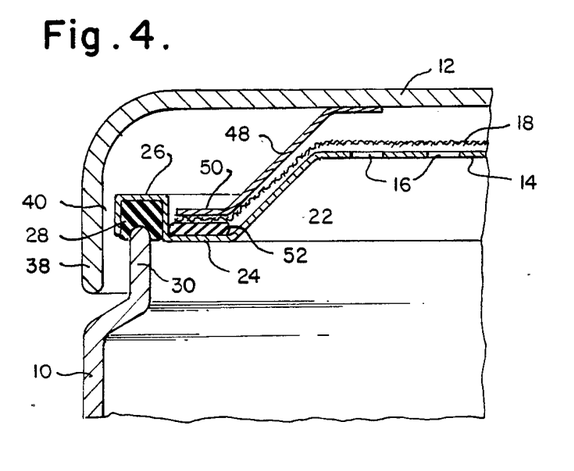
FIG. 4 is an enlarged sectional view, also similar to FIG. 2, of a portion of another sterilization container.
Figure 5:
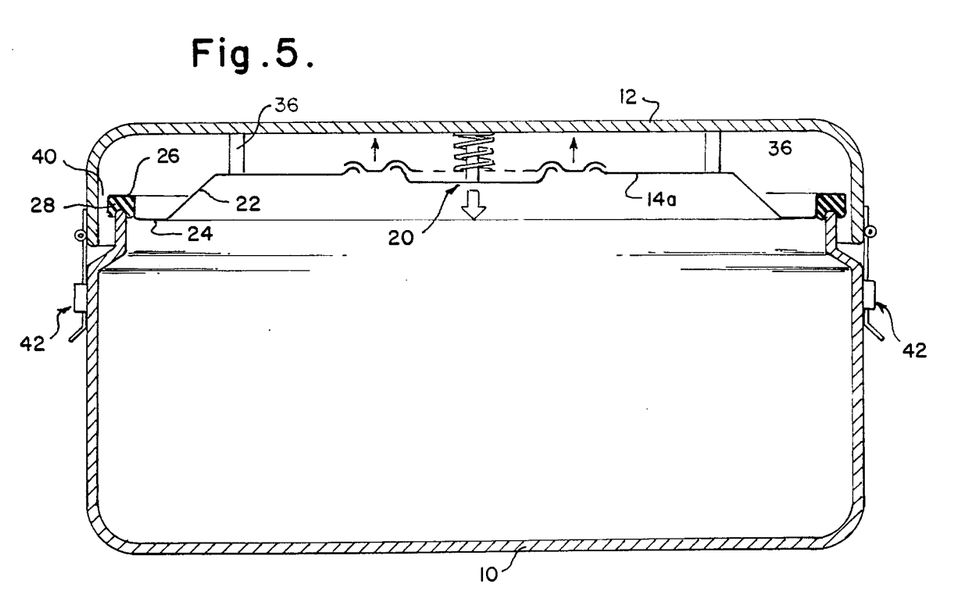
FIG. 5 is a sectional view of a sterilization container having a two-way valve.

In the container shown in FIG. 4, a rigid frame 48, of similar configuration to spring plate 44, is attached to outer cover 12. Rigid frame 48 is configured to parallel inclined transition segment 22 and flat segment 24. Flat segment 24 of intermediate cover 14 has a flat sealing member 52 attached to its upper surface. In an assembled condition, flat sealing member 52 presses the edge of filter material 18 against the underside of flat peripheral segment 50 to prevent the passage of microbial contamination underneath filter material 18.

It thus may be seen that when outer cover 12 carrying intermediate cover 14, with filter 18, or intermediate cover 14a, with valve 20, is latched onto container base portion 10, sealing ring 28 forms a seal with edge 30 of base portion 10 and the interior of container base portion 10 is sealed off against the passage of microbial contamination.

It will be appreciated by those skilled in the art that the annulus 40 formed between outer cover 12 and the upper edges 30 of container base portion 10 will be dimensioned to permit the flow of media during all conditions, pressure or vacuum, that may be applied within a sterilizer during a sterilization cycle. The construction features of the containers just described assure that the media exchange will take place only through filter 18, in the case of the container shown in FIGS. 1–4, or only through valve 20, in the container shown in FIG. 5. These filters or valves are protected against influences from the outside by reason of the presence of overlapping outer cover 12.

Figure 6:
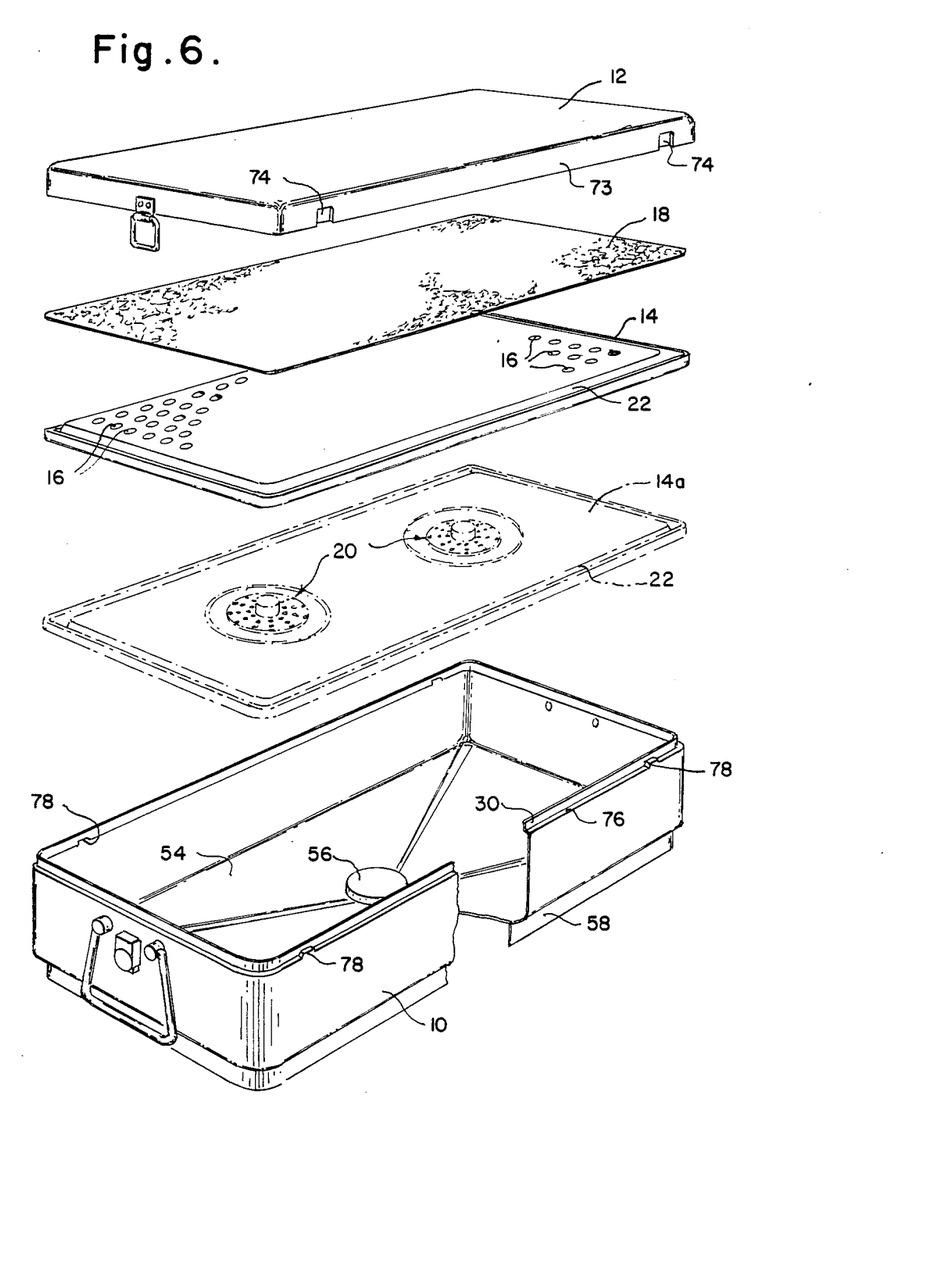
FIG. 6 is an exploded isometric view of a sterilization container illustrating interchangeable intermediate covers.

FIG. 6 highlights the interchangeable nature of intermediate cover 14, which is perforated and is used in conjunction with filter material 18, and intermediate cover 14a, which is solid and includes at least one two-way valve 20. FIG. 6 also illustrates a preferred construction of container base portion 10 that includes a drain valve 56 in the floor 54 of container base portion 10. Preferably, the floor 54 is sloped downwardly in a funnel-like manner so that any condensate present within container base portion 10 can flow to drain valve 56 and be discharged therefrom. A still further preferred construction feature of container base portion 10 is illustrated in FIG. 6; namely, the presence of a peripheral base flange 58. Base flange 58 offers a number of advantages;

(1) With the floor 54 of container base portion 10 being constructed in sloping fashion, base flange 58 provides stability when container base portion 10 rests on a flat surface;

(2) Base flange 58 provides an air space between any supporting surface and floor 54 of container base portion 10 and thereby reduces the likelihood of condensate formation within container base portion 10 when it is placed on a relatively cold surface;

(3) Base flange 58 supports container base portion 10 so that drain valve 56 is out of contact with any supporting surface and thereby the likelihood of physical damage to drain valve 56 is minimized; and (4) Base flange 58 registers with the upstanding lugs formed at the corners of outer cover 12 (see FIGS. 9–12) and affords a degree of alignment when the sterilizer containers are stacked.

Drain valve 56 may be of any well-known construction that opens during the sterilization cycle and closes before the sterilizer chamber is opened. Especially suited for use in the present invention as drain valve 56 is the valve described in Austrian Pat. No. 5856/80 (and corresponding West German Patent Application No. P 32 02 430.4). This latter valve has a valve disk which is carried by a bimetallic strip biased by a closing spring; in the closed position, the valve disk contacts the edge of a valve seat and is lifted from this position into the open position against the action of the closing spring upon the occurrence of temperature dependent deflection of the bimetallic strip. When the temperature falls, the bimetallic strip straightens to permit the closing spring to exert sealing pressure on the valve disk against its seat.

Figure 7:
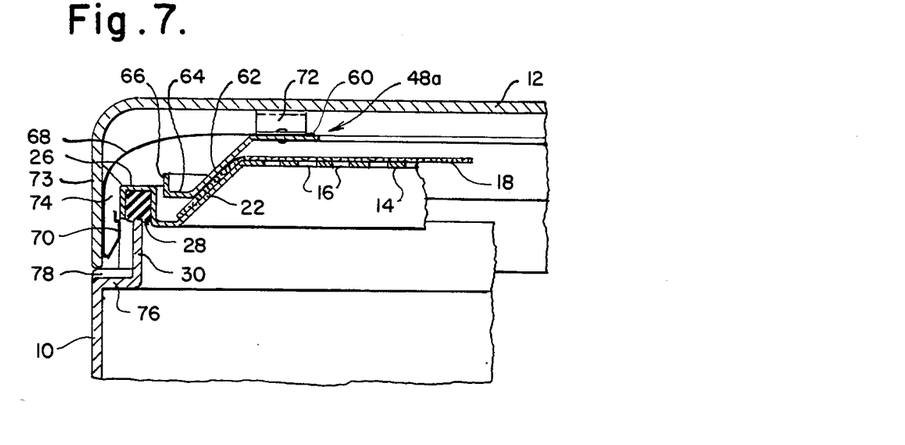
FIG. 7 is a sectional view, similar to FIGS. 2–4, of a portion of a sterilization container of the type shown in FIG. 6.
Figure 8:
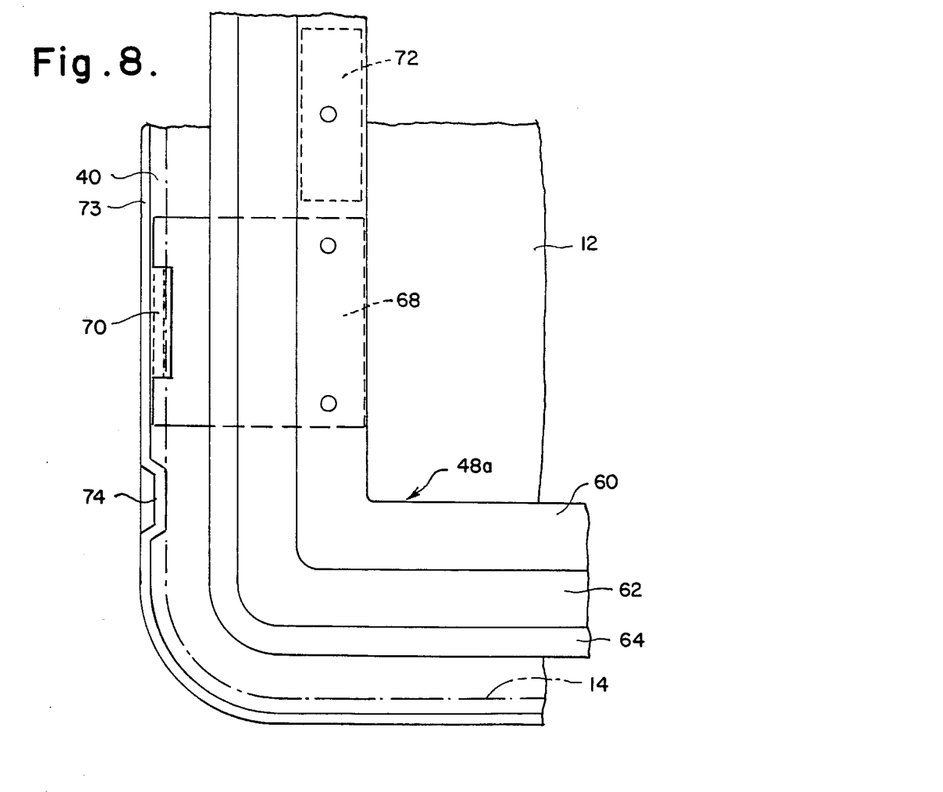
FIG. 8 is a bottom plan view of a portion of the sterilization container shown in FIG. 6.
Figure 9:
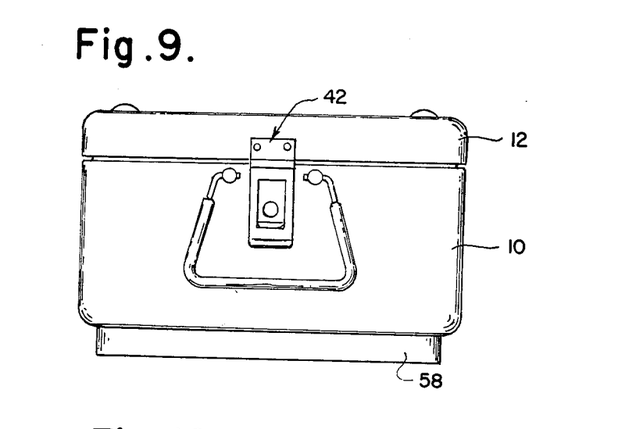
FIG. 9 is an end elevational view of the sterilization container shown in FIG. 6.
Figure 10:
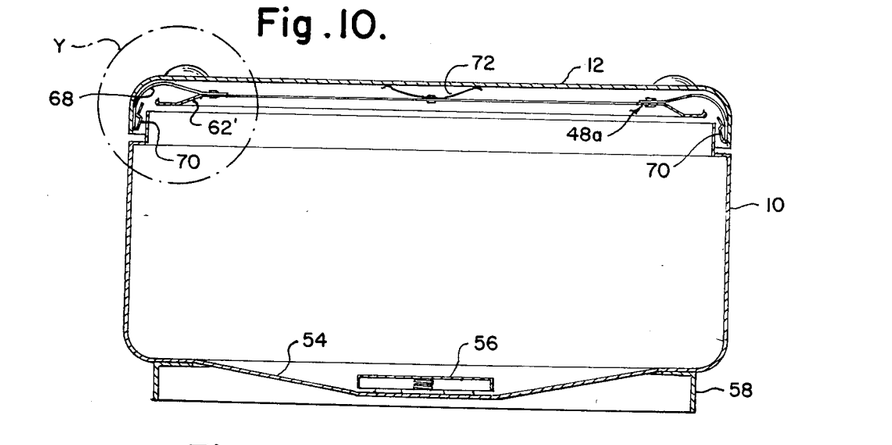
FIG. 10 is a sectional view of the sterilization container of FIG. 9 without an intermediate cover.
Figure 11:
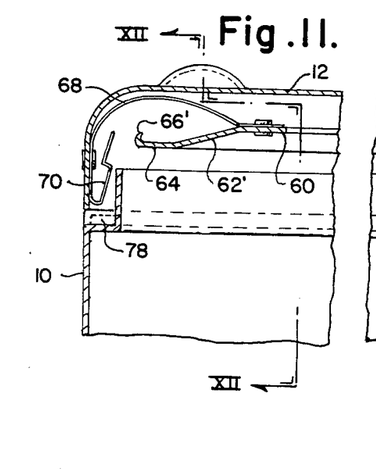
FIG. 11 is an enlarged sectional view of that portion o the sterilization container shown in FIG. 10 located within the circle y.
Figure 12:
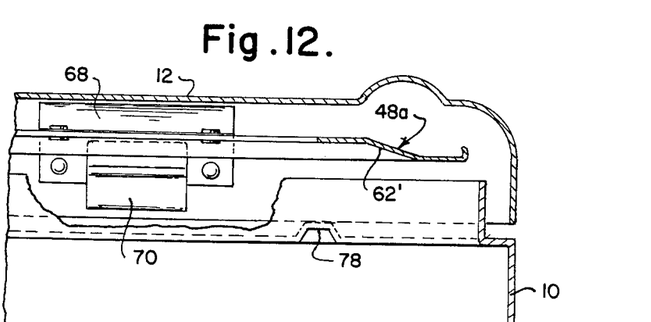
FIG. 12 is a sectional view taken along the line XII—XII of FIG. 11.
Figure 13:
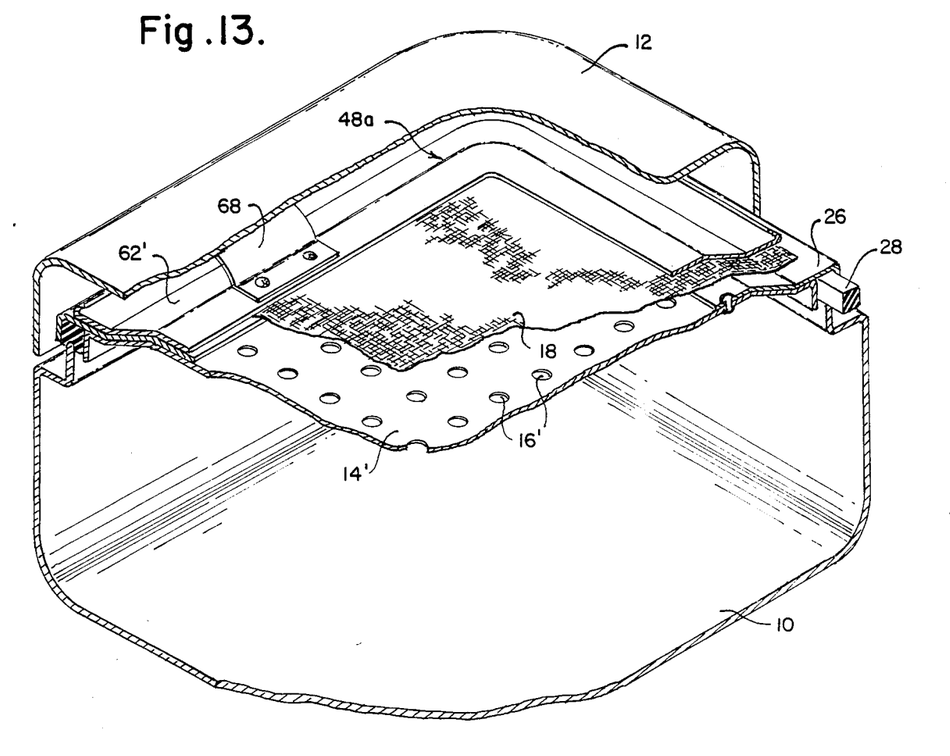
FIG. 13 is a partial isometric view, with portions broken away, of a sterilization container having a perforated intermediate cover and a filter.
Figure 14:
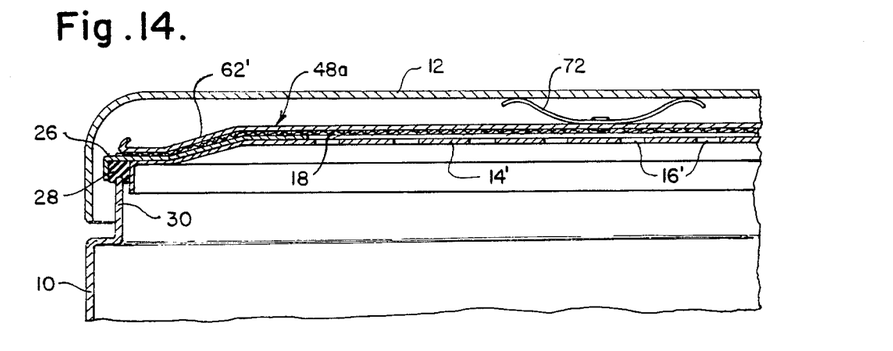
FIG. 14 is a partial sectional view of the sterilization container of FIG. 13 viewed from the left.

The container shown in FIG. 6, which advantageously permits interchangeability of intermediate cover 14 with filter material 18 and of intermediate cover 14a with valves 20, will now be described by reference to FIGS. 7–17. Referring specifically to FIGS. 7–8, a peripheral frame 48a is disposed within outer cover 12 and consists of a sheet metal section which has an inner horizontal segment 60, an inclined transition segment 62 extending downwardly and outwardly at approximately 45°, and a horizontally extending outer segment 64 which terminates in an upwardly extending flange portion 66. Frame 48a is carried inside outer cover 12 by leaf springs 68 which are either welded or riveted at one end to the sidewalls 73 of outer cover 12 and welded or riveted at the other end to the inner segment 60 of frame 48a. The portion of leaf spring 68 contacting the sidewall 73 of outer cover 12 is bent inwardly and downwardly to terminate in a locking hook 70 which, with intermediate cover 14 in place, is positioned under the outer leg of inverted U-shaped segment 26 of intermediate cover 14; in this position, inclined transition segment 22 of intermediate cover 14 abuts transition segment 62 of support frame 48a. The engagement of inverted U-shaped segment 26 of intermediate cover 14 against locking hook 70 is effected by leaf springs 72 which are welded or riveted at their central portions to horizontal segment 60 of support frame 48a; leaf springs 72 are rounded at their two extending feet which contact the lower surface of outer cover 12 and thus serve to bias frame 48a downwardly away from outer cover 12. The sidewalls 73 of outer cover 12 are provided with inwardly extending recesses 74 which tend to center intermediate cover 14 (or 14a) within outer cover 12 and further tend to center the sidewalls 73 of outer cover 12 relative to container base portion 10 by contact of the walls of the recesses 74 with the outer edge of inverted U-shaped segment 26 of intermediate cover 14 (or 14a). In order to preserve the vertical spacing between the sidewalls 73 of outer cover 12 and the upper edges 30 of container base portion 10, ledge 76, which is formed beneath upper edge 30 of container base portion 10, has lugs 78 which register with recesses 74 when outer cover 12 is in place.

As shown in FIG. 7, an intermediate cover 14 with a filter cloth 18 is clamped into outer cover 12 as described above, with transitional inclined segments 22 and 62 of intermediate cover 14 and support frame 48a, respectively, matching and abutting one another. It will be readily apparent that in substitution for this arrangement, intermediate cover 14a with its valves 20 could be clamped within outer cover 12 by means of locking hooks 70.

Figure 15:
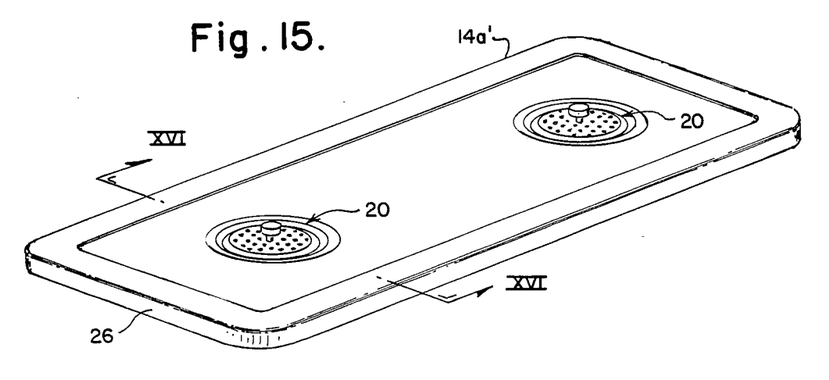
FIG. 15 is an isometric view of an intermediate cover having two-way valves.
Figure 16:
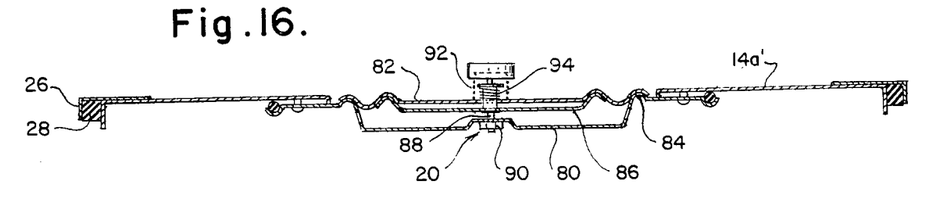
FIG. 16 is a sectional view taken at the plane XVI—XVI of FIG. 15.

The container shown in FIGS. 10–14, differs from the previous containers in that the transitional segment 62' of support frame 48a is made flatter to better match the surfaces of intermediate cover 14'. As shown in FIGS. 15–16, intermediate cover 14a' which is provided with valves 20 is removably clamped within outer cover 12 in the same manner as described for intermediate cover 14 of FIGS. 7-8 in that intermediate cover 14a' is pressed against frame 48a so that locking spring 70 can snap into position.

Figure 17:
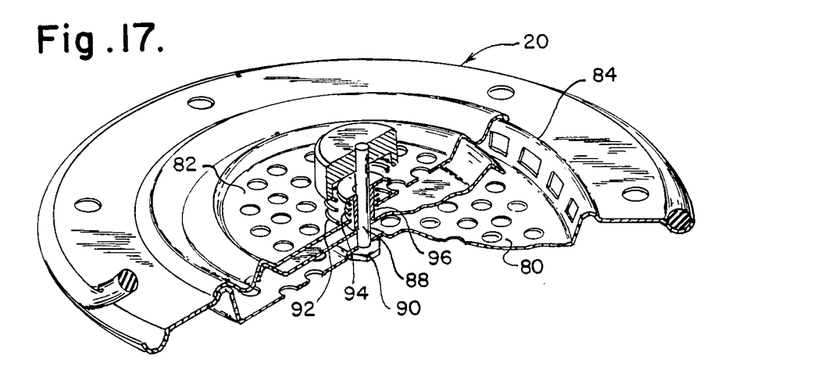
FIG. 17 is a partial isometric view, with portions broken away, of one of the valves shown in FIG. 15.
Figure 18:
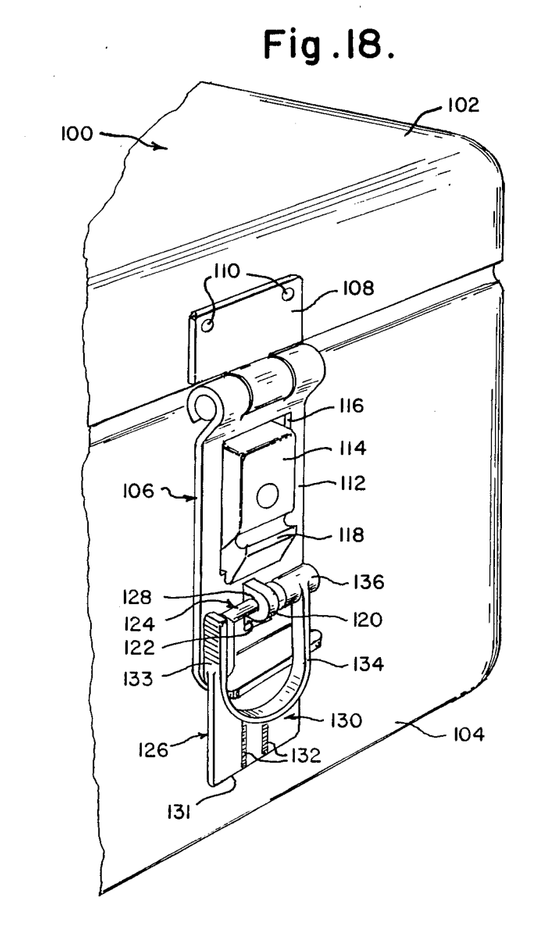
FIG. 18 shows a portion of a preferred embodiment of the present invention having a seal post which passes through the container latch and through which the seal passes.

As shown in FIGS. 16 and 17, valve 20 of intermediate cover 14a, 14a' is a double acting closure valve which is pressure actuated. Valve 20 includes a perforated inner plate 80, a perforated outer plate 82 which abuts on a bead 84, and an inner valve plate 86; these plates are held together by means of bolt 88 and nut 90 on which a compression coil spring 92 is positioned between plate 82 and the head of bolt 88; through spring 92, outer plate 82 is pressed onto its bead seat 84. A further compression coil spring 94 is drawn over a post 96, which is fixed to valve plate 86, and spring 94 is supported between plate 82 and the head of post 96, thereby pressing valve plate 86 upwardly against plate 82.

The preferred embodiments shown in FIGS. 18, 19, 20 and 29 employ, preferably, one of the sterilizer containers shown in FIGS. 1 through 17. Outer cover or closure 102 of sealed sterilizer container 100, shown in FIG. 18, can be fastened to container base or receptacle 104 by a tension lock 106. Tension lock 106 includes a base portion 108 secured to cover 102 with a pair of rivets 110. A latch 112 is hinged in the conventional fashion to base portion 108. Operator 114 is slidingly secured to base 104 and is adapted to be received by a generally rectangular opening 116 formed in latch 112. Operator 114 defines a catch 118 which is adapted to engage latch 112 in the conventional fashion. Longitudinal movement of operator 114 enables catch 118 to prevent or allow latch 112 to be swung away from the latched position shown in FIG. 18. A seal post 120 is secured to base 104 and so positioned that it extends through an opening 122 defined by latch 112 when latch 112 is in the latched position. Fracturable member 124 of indicator seal 126 is inserted through opening 128 defined by seal post 120. Indicator seal 126 is sealed by inserting locking member 137 into locking passage 135 until end 138 exits passage 135. Authorized opening of container 100 is usually preceded by manual breaking of fracturable member 124. In any event, when operator 114 is moved toward cover 102 and latch 112 is swung away from base 104, latch 112 breaks fracturable member 124 and a visual indication is provided that the articles disposed within container 100 are contaminated.

Figure 19:
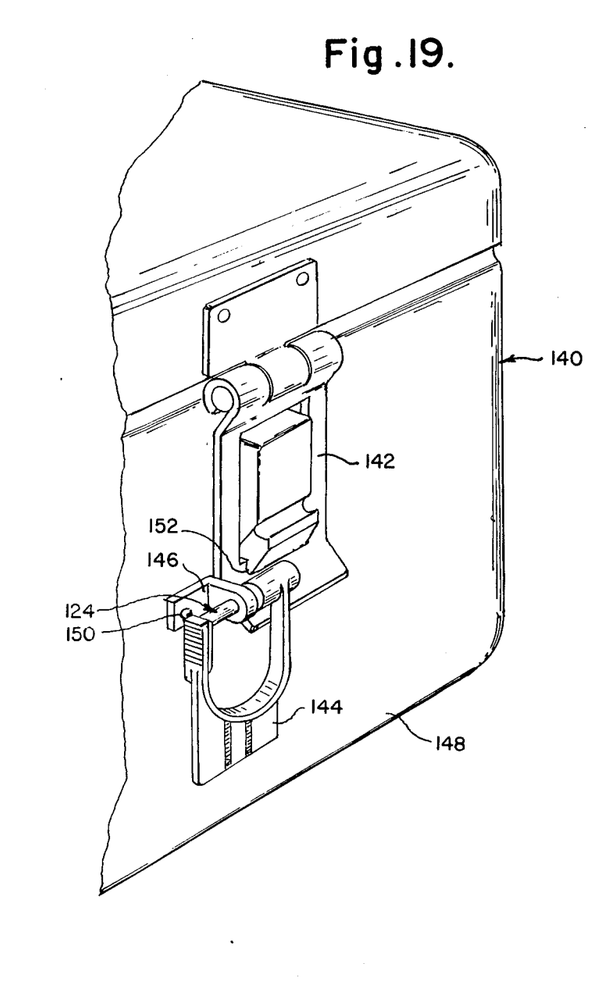
FIG. 19 shows a portion of a preferred embodiment of the present invention which includes a seal post mounted beside the container latch and through which the seal passes, the seal being broken when the latch is raised to open the container.

FIG. 19 shows a sealed sterilization container 140, another preferred embodiment of the present invention. Sealed sterilization container 140 is identical to sealed sterilization container 100, with the exception of the configuration of latch 142 and the mounting arrangement of indicator seal 144 with respect to latch 142. The fracturable member 124 of indicator seal 144 is so mounted that it overlaps edge 152 of latch 142. Latch 142 is identical to latch 112 with the exception that latch 142 does not define an opening to receive a seal post. Rather, seal post 146 is mounted to base 148 adjacent latch 142 with a rivet 150. Accordingly, edge 152 of latch 142 fractures fracturable member 124 when latch 142 is swung away from base 148.

Figure 20:
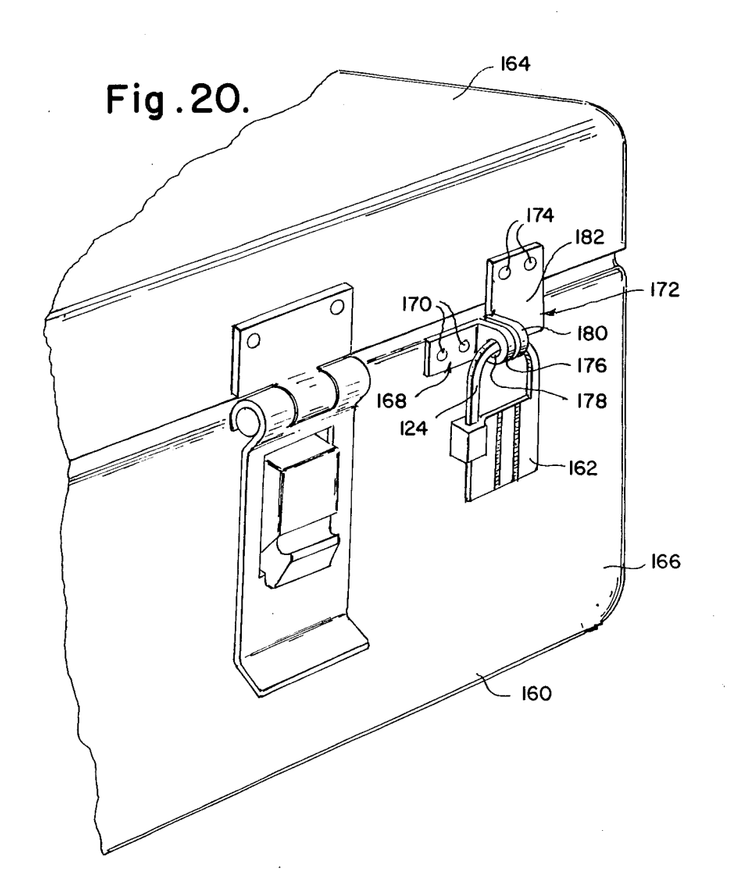
FIG. 20 shows a portion of a preferred embodiment of the present invention with two seal posts, one post being mounted to the closure and the remaining post being mounted to the receptacle through both of which the seal passes.
Figures 21, 25, 26, 27, 28:
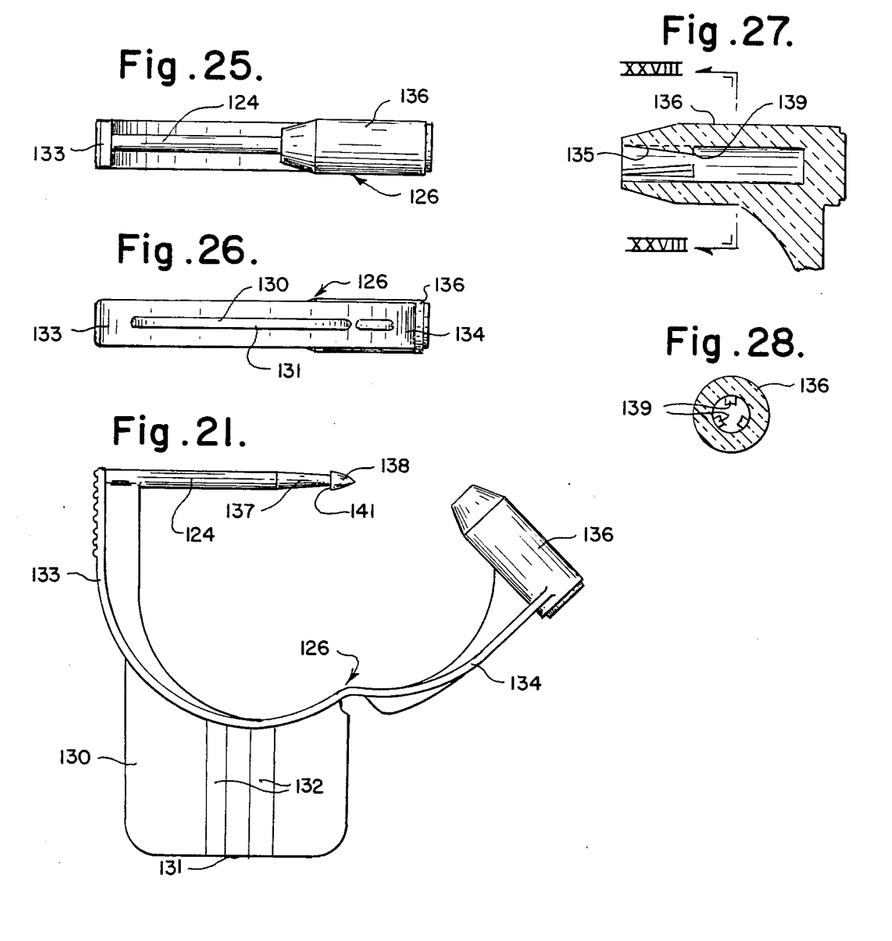
FIG. 21 shows a preferred embodiment of the indicator seal of the present invention, in the unlocked position.
FIG. 25 is a top elevational view of the indicator seal shown in FIG. 22.
FIG. 26 is bottom view of the indicator seal shown in FIG. 22.
FIG. 27 is a sectional view of a portion of the indicator seal shown in FIG. 25.
FIG. 28 is a sectional view of the portion of the indicator seal shown in FIG. 27 taken along the line XXVIII—XXVIII.
Figures 22, 23:
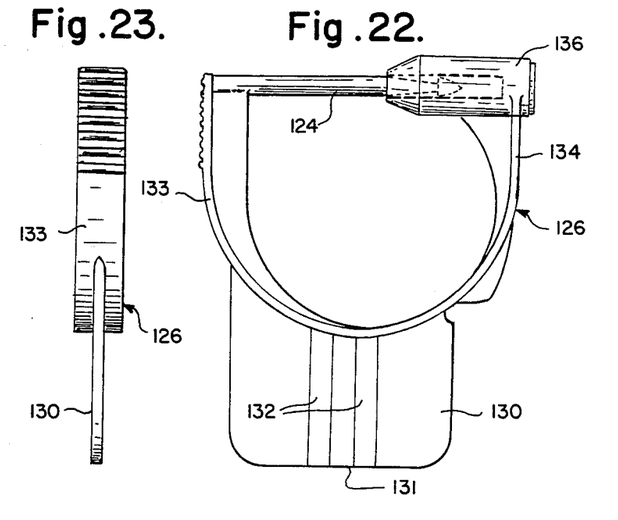
FIG. 22 shows the indicator shown in FIG. 21, in the sealed position.
FIG. 23 is a left side elevational view of the indicator seal shown in FIG. 22.
Figure 24:
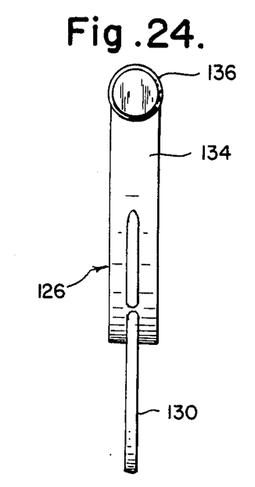
FIG. 24 is a right side elevational view of the indicator seal shown in FIG. 22.

FIG. 20 shows sealed sterilizer container 160, another preferred embodiment of the present invention. Sterilizer container 160 is identical to containers 100 and 140, with the exception of the mounting arrangement of indicator seal 162. Seal 162 is so mounted to container 160 that fracturable member 124 will be fractured when outer cover 164 is moved toward a contaminating position, that is, when outer cover 164 is opened to such an extent that microbial life can enter the interior of container 160 between cover 164 and base 166. A seal post 168, which can be identical to seal posts 120 and 146, is mounted to base 166 near its top with a pair of rivets 170. A second seal post 172 is mounted near the bottom of outer cover 164 with a pair of rivets 174. Seal post 168 includes a flanged portion 176 which defines an opening 178. Seal post 172 includes a flanged portion 180 which defines a similar opening (not shown). Seal posts 168 and 172 are so mounted to base 166 and outer cover 164, respectively, that opening 178 of seal post 168 and the opening defined by flanged portion 180 of seal post 172 confront each other and permit fracturable member 124 of indicator seal 162 to be passed therethrough before indicator seal 162 is sealed. Accordingly, fracturable member 124 must be broken to move outer cover 164 to a contaminating position.

Figure 29:
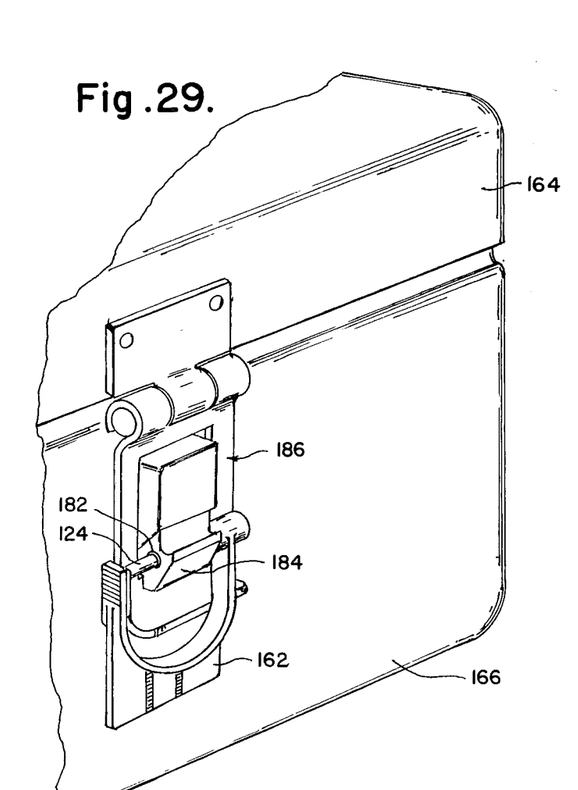
FIG. 29 shows a portion of a preferred embodiment of the present invention which does not require a seal post.

Alternately, as is shown in FIG. 29, seal posts 168 and 172 of container 160 can be eliminated and fracturable member 124 of seal 162 can be passed through a bore 182 defined by operator 184 before seal 162 is secured. When seal 162 is so mounted to operator 184, fracturable member 124 must be broken by hand or by latch 186 to move cover 164 to a contaminating position.

What is claimed is:

1. A disposable seal comprising a body portion and a resilient fracturable portion having two ends, said fracturable portion being connected to said body portion at one end and being free at the remaining end, said body portion defining a socket for receiving said remaining end, said socket and said remaining end being so configured that said remaining end can be inserted into and locked within said socket to lock said seal, unlocking said seal requiring the fracturing of said fracturable portion thereby destroying the utility of said seal as a seal, said body portion comprising an indicator portion that includes a sterilization indicator.

2. A container for holding articles while they are being subjected to a sterilization process, for storing the articles subsequent to the completion of the sterilization process, and for maintaining the degree of sterilization of the articles achieved during the course of the sterilization process, comprising:
- a receptacle for receiving and supporting articles while they are being sterilized and stored;
- a closure means associated with said receptacle which is capable of assuming an opened position in which access can be had to said receptacle to permit said receptacle to receive articles and to permit removal of articles from said receptacle, and a closed position in which said access cannot be had; said closure means comprising means for permitting the flow of sterilant into said receptacle while preventing the entry of microbial life into said receptacle when said closure means is in its closed position;
- a disposable sealing member for sealing said closure means in its said closed position, said sealing member comprising a fracturable portion, said sealing member being capable of being unsealed after it is sealed only by destroying the utility of said sealing member as a seal wherein fracturing said fracturable portion causing the utility of said sealing member as a seal to be destroyed, said sealing member being so secured to said container that movement of said closure means from its said closed position to an opened contaminating position, in which microbial life can enter said receptacle, requires fracturing said sealing member thus causing said sealing member to lose its utility as a seal; and
- said sealing member further comprising an indicator portion that includes a sterilization indicator.

3. The container recited in claim 1 wherein said sealing member is constructed of plastic.

* * * * *

UNITED STATES PATENT AND TRADEMARK OFFICE
CERTIFICATE OF CORRECTION

PATENT NO. : 4,562,047
DATED : December 31, 1985
INVENTOR(S) : Joseph T. Sestak and Jonathan Kagan It is certified that error appears in the above—identified patent and that said Letters Patent is hereby corrected as shown below:

Col. 4, line 8, delete "129" and substitute therefor --139--.

Signed and Sealed this

Sixth Day of May 1986

[SEAL]

Attest:

DONALD J. QUIGG

Attesting Officer

Commissioner of Patents and Trademarks